United States Patent
Hansen

(10) Patent No.: US 8,470,219 B2
(45) Date of Patent: Jun. 25, 2013

(54) METHOD FOR THE PRODUCTION OF A FIBROUS WEB FROM CELLULOSE FIBERS IN AN AIR-LAID PROCESS

(75) Inventor: Morton Rise Hansen, Aalborg (DE)

(73) Assignee: Glatfelter Falkenhagen

( * ) Notice: Subject to any disclaimer, the term of this patent is extended or adjusted under 35 U.S.C. 154(b) by 247 days.

(21) Appl. No.: 10/590,748

(22) PCT Filed: Feb. 16, 2005

(86) PCT No.: PCT/EP2005/001552
§ 371 (c)(1),
(2), (4) Date: Nov. 20, 2006

(87) PCT Pub. No.: WO2005/080655
PCT Pub. Date: Sep. 1, 2005

(65) Prior Publication Data
US 2007/0209768 A1    Sep. 13, 2007

(30) Foreign Application Priority Data
Feb. 25, 2004 (DE) .......... 10 2004 009 556

(51) Int. Cl.
*D04H 1/48* (2006.01)
*D04H 1/00* (2006.01)

(52) U.S. Cl.
USPC .......... 264/128; 264/109; 264/119; 264/121; 264/517; 156/62.2; 156/78; 156/209; 162/115; 162/169; 428/156; 428/340

(58) Field of Classification Search
USPC .......... 156/62.2, 78, 209, 219, 296; 264/109, 264/112, 115, 119, 121–122, 128, 517–518; 162/109, 117, 158, 164.1, 169, 115; 428/156, 428/340
See application file for complete search history.

(56) References Cited

U.S. PATENT DOCUMENTS

| | | | | |
|---|---|---|---|---|
| 3,575,749 A | * | 4/1971 | Kroyer | 156/62.2 |
| 3,663,348 A | * | 5/1972 | Liloia et al. | 428/171 |
| 3,669,778 A | * | 6/1972 | Rasmussen | 156/62.2 |
| 3,692,622 A | | 9/1972 | Dunning | |
| 4,057,669 A | * | 11/1977 | McConnell | 428/152 |
| 4,096,311 A | * | 6/1978 | Pietreniak | 442/59 |
| 4,127,637 A | * | 11/1978 | Pietreniak et al. | 264/119 |

(Continued)

FOREIGN PATENT DOCUMENTS

| | | |
|---|---|---|
| EP | 0 033 988 | 1/1981 |
| FR | 2 138 296 | 1/1973 |

(Continued)

OTHER PUBLICATIONS

First Examination Report, Government of India, Patent Office dated Jul. 20, 2011.

*Primary Examiner* — Jose A Fortuna
(74) *Attorney, Agent, or Firm* — Beck & Tysver PLLC

(57) ABSTRACT

Method for producing a fibrous web exclusively from cellulose fibers of natural origin, comprising the following procedural steps:
  forming an essentially uniformly thick, dry fiber layer from loose fibers having a low moisture content,
  pressing and embossing the fiber layer to obtain a fibrous web and forming an embossed pattern,
  moistening the fibrous web with a water-latex mixture having a high water concentration (75 to 99% by weight of water) and precipitating the latex in a drying process while the fibers are bonded inside and outside the fiber bond zones.

22 Claims, 3 Drawing Sheets

U.S. PATENT DOCUMENTS

| | | | |
|---|---|---|---|
| 4,134,948 A * | 1/1979 | Baker, Jr. | 264/518 |
| 4,135,024 A * | 1/1979 | Callahan et al. | 428/171 |
| 4,157,236 A * | 6/1979 | Busker et al. | 425/174.8 E |
| 4,159,355 A * | 6/1979 | Kaufman | 427/209 |
| 4,292,271 A | 9/1981 | Buob et al. | |
| 4,296,161 A * | 10/1981 | Kaiser et al. | 428/171 |
| 4,370,289 A * | 1/1983 | Sorenson | 264/113 |
| 4,425,126 A * | 1/1984 | Butterworth et al. | 604/366 |
| 4,640,810 A * | 2/1987 | Laursen et al. | 264/518 |
| 5,128,082 A * | 7/1992 | Makoui | 264/112 |
| 5,378,528 A * | 1/1995 | Makoui | 428/219 |
| 5,389,202 A * | 2/1995 | Everhart et al. | 162/103 |
| 6,041,701 A * | 3/2000 | Louis Dit Picard et al. | 101/6 |
| 6,332,996 B1 * | 12/2001 | Dit Picard et al. | 264/280 |
| 6,784,126 B2 * | 8/2004 | Everhart et al. | 442/401 |
| 6,893,525 B1 * | 5/2005 | Schmidt et al. | 156/209 |
| 7,037,394 B2 * | 5/2006 | Christensen et al. | 156/78 |
| 7,208,064 B2 * | 4/2007 | Schmidt et al. | 156/209 |
| 2002/0066517 A1 * | 6/2002 | Christensen et al. | 156/79 |
| 2003/0157856 A1 * | 8/2003 | Schroeder et al. | 442/123 |
| 2005/0039846 A1 * | 2/2005 | Schmidt et al. | 156/209 |
| 2005/0112980 A1 * | 5/2005 | Strandqvist et al. | 442/416 |
| 2005/0118916 A1 * | 6/2005 | Ducker et al. | 442/385 |
| 2006/0008621 A1 * | 1/2006 | Gusky et al. | 428/156 |
| 2007/0056674 A1 * | 3/2007 | Sellars | 156/62.2 |
| 2007/0178795 A1 * | 8/2007 | Stralin et al. | 442/408 |
| 2007/0209768 A1 * | 9/2007 | Morton Rise | 162/146 |
| 2007/0266503 A1 * | 11/2007 | Schmidt-Forst et al. | 8/131 |
| 2009/0123707 A1 * | 5/2009 | Skoog et al. | 428/172 |

FOREIGN PATENT DOCUMENTS

| | | |
|---|---|---|
| JP | 2007500104 | 6/2011 |
| WO | 9410957 | 5/1994 |
| WO | WO 99/25281 | 5/1999 |
| WO | 9963923 | 12/1999 |
| WO | 0041882 | 7/2000 |
| WO | 0059439 | 10/2000 |
| WO | WO 0071790 A1 * | 11/2000 |
| WO | WO 2005080655 A1 * | 9/2005 |

* cited by examiner

VE 150.200 (no SAP) magnitude 11x

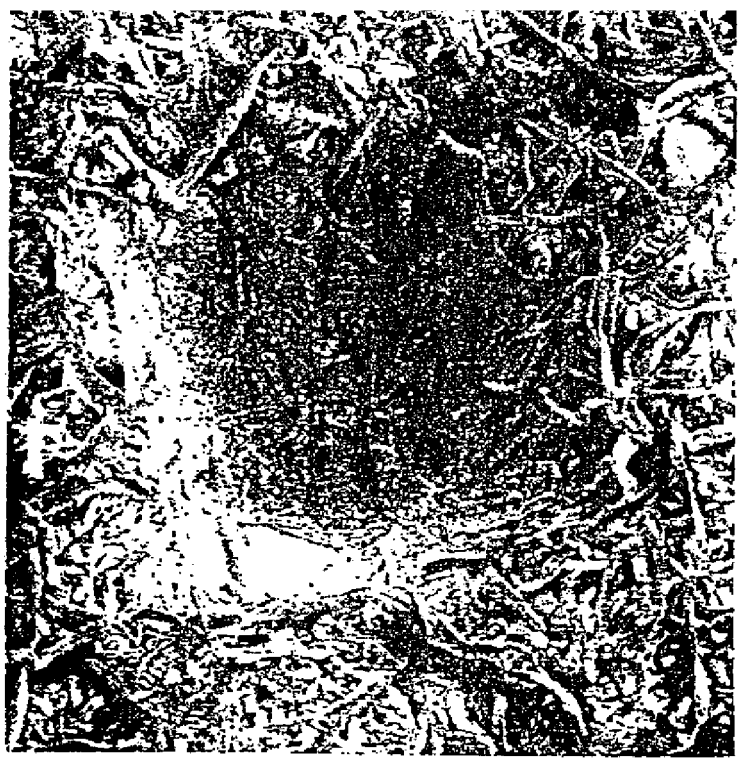
VE150.200 magnitude 50x, embossed dot
VE150.200 magnitude 500x, squeezed pulp

METHOD FOR THE PRODUCTION OF A FIBROUS WEB FROM CELLULOSE FIBERS IN AN AIR-LAID PROCESS

CROSS-REFERENCE TO RELATED APPLICATIONS

This application is a national stage filing of and claims priority to PCT/EP2005/001552, filed, Feb. 16, 2005 and claims priority to German Patent Application 10 2004 009 556.6, filed Feb. 25, 2004.

BACKGROUND OF THE INVENTION

The invention relates to a method for the production of a fibrous web from cellulose fibers having absorbing properties in an air-laid process. Moreover, the invention relates to a fibrous web which is produced according to the aforementioned method. Fibrous webs according to the invention should be suitable for the production of hygiene articles, in particular for incontinence articles, disposable diapers, panty liners or sanitary napkins, whereby they essentially serve as absorbing core for the aforementioned hygiene articles. Absorbent liners for food packages are a further use. Further applications in which the use of cellulose fibers is important while avoiding other fibrous material are known to an expert in the field.

The production of fibrous webs from cellulose fibers in air-laid processes in which, unlike in the wet-laid process, the fibers are placed on a conveyor belt in an air current and compacted by press rolls has been known for many years.

Cellulose fibers that can be used for hygiene products include, in particular, so-called "fluff pulp" fibers which are obtained from northern softwood or from American southern pine. The average fiber length of cellulose fibers of this type is about 2.4-2.8 mm. The absorbency of the loosely compacted dry fibers is about 10-12 g liquid per gram fibers. Corresponding data is found in WO 9316228 (Norlander), Table 2, for untreated reference material or in WO 8804704 (Graef), Table 7. It is known to insert further absorbing material into the fiber matrix; in particular, in this connection, so-called superabsorbent polymers (SAP) are known that have an absorbing capacity that is substantially greater than 10 g liquid per gram polymers, which are also produced in a fibrous form (SAF=superabsorbent fibers).

The U.S. Pat. No. 3,692,622 describes an absorbent fiber bond in the form of a cellulose fibrous web for producing paper towels, whereby the web is provided with a predetermined embossed pattern. The fibrous web is a continuum of drained, essentially unbound fibers having a length of less than 1.27 cm which are interconnected to form a coherent web by embossings, which cover 5 to 40% of the web surface and have a smaller distance from one another than corresponds to the length of the individual fibers, such that the thickness in the non-embossed areas is at least 2.5 times as great as in the embossed areas.

In fibrous webs which consist exclusively of cellulose fibers, it is a problem to bring the absorbency to a high level and, at the same time, keep the formation of dust low. It is in fact known to produce fibrous webs having fusible synthetic fibers, also so-called bicomponent fibers, and to provide them with a low dust content. However, the partial object of the invention is to dispense with synthetic fiber admixtures of this type. Rather, a fibrous web produced from cellulose fibers should be obtained in which the dust due to fluff, the so-called dust range, is below 0.1% of the starting web. The use of latex binders should thereby be maintained at a low level, i.e. the areal weight in the dry state should be in the range of less than 5 g/m$^2$.

SUMMARY OF THE INVENTION

This object, i.e. in particular the prevention of the fiber dust "linting", is solved by a method for the production of a fibrous web from cellulose fibers having absorbing properties in a draining process comprising the following procedural steps:
  forming an essentially uniform dry fiber layer from loose fibers having a low moisture content that is in the range of residual moisture,
  pressing and embossing the fiber layer to obtain a fibrous web and form an embossed pattern with compact fiber bond zones in which the fibers are essentially interconnected while self-bonding,
  moistening the fibrous web with a water-latex mixture having a high water concentration on at least one of the outer zones,
  precipitating the latex in a drying process while bonding the fibers inside and outside the fiber bond zones.

BRIEF DESCRIPTION OF THE SEVERAL VIEWS OF THE DRAWINGS

FIG. 3 is a micrograph of a section of the web manufactured in accordance with the invention; and, FIG. 4 is a micrograph of a section of the web manufactured in accordance with the invention.

DETAILED DESCRIPTION OF THE INVENTION

Figure 1:
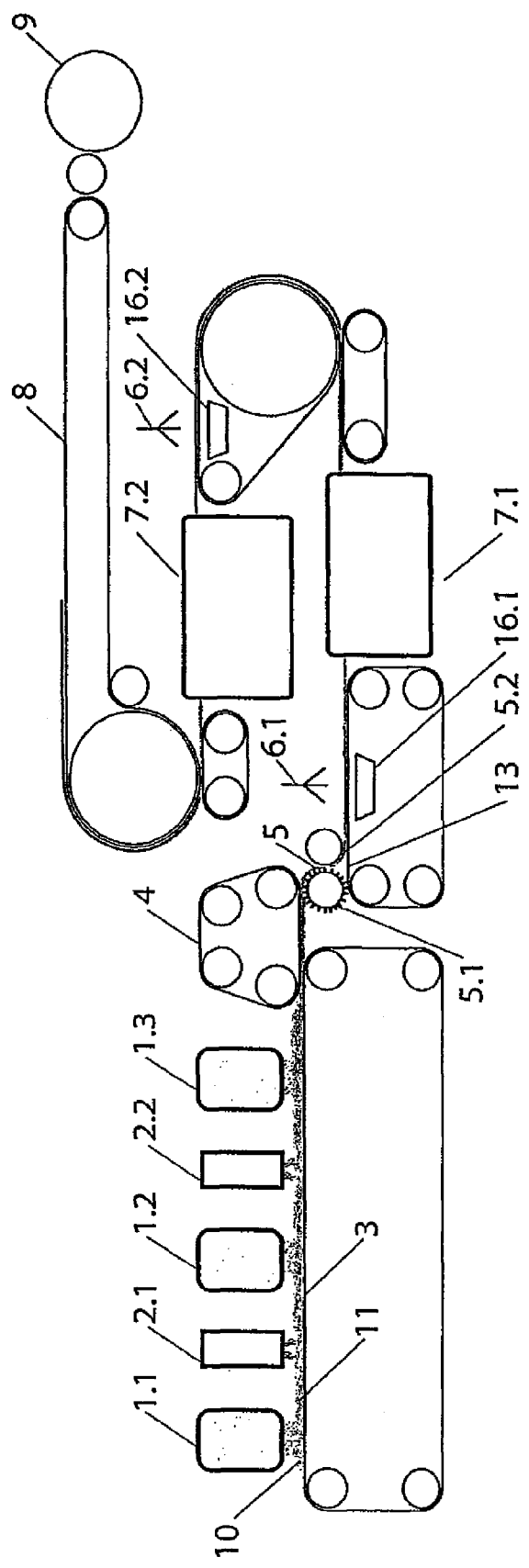
FIG. 1 is a schematic representation of the structure of a machine for practicing the method of the invention.

The "fluff pulp" fibers sold by manufacturers such as Weyerhaeuser or Tartas are suitable as cellulose fibers, which are delivered in compact rolls and are again treated to obtain a fibrous wadding and individual fibers by means of hammer mills. The fiber lengths of the fibers to be processed into the form of fibrous webs is, depending on the starting material, in the order of 2.0 to 3.0 mm, preferably 2.3 to 2.8 mm.

The use of latex to bind fibers is fundamentally known. Generally, latex is only used to obtain a binding of unembossed cellulose fiber webs. However, it was shown that by forming an embossed pattern with compacted fiber bond zones, in which the fibers are essentially interconnected by self-bonding, together with a latex bond present in the outer regions of the fibrous web is sufficient to substantially suppress the fiber dusts, also called "linting" or fluff. The term "residual moisture" refers to the natural moisture in the cellulose fibers after their production.

The term "self bonding" is to refer to the tendency known in cellulose fibers to enter into a bonding under high pressure and without moisture that is previously supplied.

A water-latex mixture with a preferably high water content being applied after the pressing process contributes to the further solidification, whereby a mixture of 90 to 99% by weight water with an addition of 10 to 1% by weight latex is generally used. The amount of the water applied is important since the water, when it evaporates, produces hydrogen bonds between the cellulose fibers.

The pressing and embossing of the fiber layer takes place in a press-roll arrangement. Preferably, at least one of the rolls is a toothed roll. In this case, the line pressure to be applied depends on the mass per unit area which the fiber layer forms; preferably, the pressures are in the range of 30 N/mm to 120 N/mm.

A negative pressure applied to the fibrous web covers the fibrous web, so that the penetration can be controlled during and/or after moistening the fibrous web with the water-latex mixture. Depending on the pulp fibers used and their average fiber length and/or areal weight of the fibrous web, a different penetration depth is required.

To increase the absorbency, fibers or granules of superabsorbent polymers (so-called SAP) are added to the fiber layer or the fibrous web prior to pressing and embossing. The superabsorbent polymers can be mixed with the fibers to be deposited or inserted into the fiber layer to obtain a layer formation.

Hydrogel-forming polymers are especially suitable as SAP, said hydrogel-forming polymers being alkali metal salts of the following organic acids: polyacrylic acid), polymethacrylic acid); copolymers of acrylic acid and methacrylic acid with acrylic amide, vinyl alcohol, acrylic ester, vinyl pyrrolidone, vinyl sulfonic acids, vinyl acetate, vinyl morpholinone and vinyl ethers; hydrolyzed, modified starches; malein anhydride copolymers with ethylene, isobutylenes, styrene and vinyl; polysaccharides, such as carboxymethyl starches, carboxymethyl cellulose and hydroxypropyl cellulose; polyacryl amides; polyvinyl pyrrolidone; polyvinyl morpholinone; polyvinyl pyridine; copolymers and mixtures of the preceding substances. The hydrogel-forming polymers are preferably cross-linked so that they become insoluble in water. In particular, a slightly cross-linked poly-Na-acrylate is used. The cross-linking can be induced by irradiation or produced by covalent, ionic or van der Waals forces and by a hydrogen bond. The superabsorbent polymers can be added in any form desired for the respective type of processing, i.e. e.g. as granules, in fiber form, as fiber groups (filaments), in flocculent form, as beads, rod-shaped or the like.

The density of the fiber bond zones depends on the required tensile strength. Usually, 16 to 49 compressed fiber bond zones per $cm^2$ are inserted into the fibrous web.

Preferably, the compressed fiber bond zones thereby cover a surface of 0.03 to 1 $mm^2$ each.

The water-latex mixture can be applied with aid of roll moistening or by spraying onto the fibrous web. The water can be dried for the precipitation of the latex with aid of radiant heat or by means of blowing warm air through the fibrous web.

The substances common in the airlaid industry can, for example, be used as latices. An example of this is an ethylene vinyl acetate emulsion which is available under the trade name AIRFLEX (Manufacturer Air Products and Chemicals Inc., Allentown, USA). Biologically degradable latices, in particular a starch-based latex, can also be used. If, in addition, the superabsorbent polymer is also produced on a biologically degradable base, then the fibrous web can be degraded in a composting step after use.

Special attention is also directed to the latex. It can be set from the start by appropriate devices in such a way that it has a hydrophilic or hydrophobic property after the precipitation and bonding of the fibrous web. Different latices can be used thereby for the opposite sides of the fibrous web. For example, for a diaper, a hydrophobic fibrous web is used on the side facing away from the body, while a hydrophilic setting is selected for the side facing the body.

The invention also relates to a fibrous web produced with a low latex bond liner in which the degree of dust is less than 0.1%, measured according to a standardized method.

A standardized method for determining the dust content in fibrous webs, as used at CONCERT GmbH, is shown as follows:

Equipment Used:

A dust testing device with a transparent, sealed chamber, having a rotating disk with two vertical rods, mounting clamps for samples, motor with a rotational speed of 150 U/min, timer, polyester film to support the samples; table sample cutter; short-term alarm clock; laboratory gloves and analytical balance AG 204 from METTLER.

Test Conditions:

The samples used for the measurement should be studied under the following ambient conditions:

Room temperature 23 degrees Celsius±2° C.

Relative humidity 50%±2%

Principle of the Determination:

The samples to be determined are clamped into the testing device and beat there for a defined period of time (shaking off the dust). The dust loss is determined by weighing the difference of the sample before and after the procedure and the dust content calculated in percent therefrom.

Carrying out the Determination:

a) Preparation of the Sample:

Samples for measuring the dust must be adapted to the aforementioned room conditions for two hours in the laboratory prior to the determination. Since the samples are hygroscopic and absorb moisture, they should, if possible, be handled with gloves to avoid affecting the results of the analysis.

b) Carrying out the Dust Determination in Sap-Free Airlaid Types:

aa) Two samples each are cut from the corresponding sample position to 125 mm×slit width (=1 sample unit) for an analysis, also a piece of polyester film of equal size.

bb) The sample unit is accurately weighed to 0.0001 g on the analytical balance after a stabilization time of 20 seconds (short-term alarm clock).

cc) The sample unit should then be inserted in a clamp in the dust testing device as follows: Both samples are to be put together congruently with the supposedly dustier sides outward, the supporting polyester film is placed on top or behind. This unit is to be mounted in the clamp about 4 to 5 cm on the short sides (the remainder protrudes upward) until the rods of the rotating disk hit the sample unit in the middle. For this purpose, the chamber door should be opened and subsequently closed again.

dd) Starting the dust tester with the switch to the right (clockwise) or to the left (counterclockwise), so that the sample (not the film) is struck first. The device runs at a speed of about 150 U/min and has a timer which automatically shuts the device off after one minute. During this time, the sample is struck about 300 times, so that any dust present falls off.

ee) After a minute, the sample is turned and mounted in the clamp with the other side. The samples are also turned thereby (the outside becomes the inside) and the side is changed in the film (in front of the samples, behind the samples). The device is then started for a further minute, but always in the opposite direction.

ff) The sample unit is then again balanced to 0.0001 g. The scales should thereby be stabilized for exactly 20 seconds.

c) Carrying out the Dust Determination in Sap-Containing Airlaid Types aaa) A sample is cut from the corresponding sample position to 125 mm×slit width for an analysis, also a piece of polyester film of equal size.

bbb) The sample unit is accurately weighed to 0.0001 g on the analytical balance after a stabilization time of about three minutes (short-term alarm clock).

ccc) The sample unit should then be inserted into a clamp in the dust testing device as follows: Both samples are to be put together congruently with the supposedly dustier sides outward, the supporting polyester film is placed on top or behind. This unit is to be mounted in the clamp about 4 to 5 cm on the short sides (the remainder protrudes upward) until the rods of the rotating disk strike the sample unit in the middle. For this purpose, the chamber door should be opened and subsequently closed again.

ddd) Starting the dust tester with the switch to the right (clockwise) or to the left (counterclockwise), so that the sample (not the film) is struck first. The device runs at a speed of about 150 U/min and has a timer which automatically shuts the device off after one minute. During this time, the sample is struck about 300 times, so that any dust present falls off.

eee) After a minute, the sample is turned and inserted in the clamp with the other side. The samples are also turned thereby (the outside becomes the inside) and the side is changed in the film (in front of the samples, behind the samples). The device is then started for a further minute, but always in the opposite direction.

fff) The sample unit is then again balanced to 0.0001 g. The scales should thereby be stabilized for exactly three minutes.

Each analysis is performed as a double determination, in that both clamps in the dust testing device are used with two similar samples (sample units) in each case.

The dust shaken off in the testing device should be removed at least after every fourth analysis.

Calculation:

$$\text{Dust }(\%)=(A-B)\bullet 100/A$$

A=weight of the sample before the test
B=weight of the sample after the test

The average values are to be calculated from the double determination.

An embodiment of the procedural sequence is described with reference to FIG. 1.

Cellulose fibers 10 having an average fiber length of 2.4 mm are continuously deposited by a hammer mill (not shown) by a first former 1.1 onto a conveyor belt 3 as loose fleece 11, so that a layer of tangled cellulose fibers is produced. This layer is still uncompressed to a large extent. A further preformed cellulose fiber layer is deposited by the former 1.2 as a layer. Finally, a third layer is placed on by the former 1.3. The individual fiber layers may also comprise different fibers and varying fiber densities. Moreover, it is possible to add superabsorbent polymers to the fibers to increase the absorption capacity. These are commercial products which have been used in the hygiene field for some time and which have already been described. The addition in layer sequence takes place via the supply bins 2.1 and 2.2. However, the superabsorbent polymer may also be added to the fibers homogeneously prior to the sprinkling.

The moisture content of the fiber-SAP mixture is given solely by the so-called residual moisture. In natural fibers, as they are used here, the residual moisture is at about 6 to 10% by weight. In the embodiment described, sodium polyacrylate in cross-linked form is used as SAP, as they are currently available on the market under the trade name Favor, Manufacturer Stockhausen GmbH & Co. KG, in particular for hygiene articles.

A precompression and conveyance to a pair of rolls 5 takes place via a conveying device 4, called "web transfer", said pair of rolls consisting of an embossing roll 5.1 and a smoothing roll 5.2 adjusted to it. The two rolls are aligned horizontally to one another. The former conveyor is not led through the rolls. The material of the rolls is steel.

The embossing roll 5.1 has embossing teeth which have comparatively steep flanks. The height of the teeth is between 0.3 and 1.0 mm. A high line pressure between the two pressure rolls ensures differences in height between the unembossed and embossed areas of at least 1:8, preferably at least 1:10. Depending on the areal weight of the fiber layer, different pressures are thereby required.

The embossing zones assume about 8 to 40% of the entire web surface. Surface parts that are too large disadvantageously affect the absorbency, while surface parts that are too small reduce the tensile strength to such an extent that it is no longer sufficient. A tensile strength of at least 15 N per 50 mm web width is strived for in the web.

In addition to the surface portion of the overall bond zone, the bond density is also important which should comprise the fiber bond zones distributed in a regular surface pattern. The distances between the individual bond zones should be less than the average fiber length. 16 to 49 compressed fiber bond zones per $cm^2$ were shown to be an advantageous value range.

During compression in the bond zones, a sufficient pressure must be produced so that the fibers in the individual bond zones can form a self-bond. With fiber layers in the range of 500 $g/m^2$, the required line pressure is about 40 N/mm; with fiber layers in the range of 150 $g/m^2$, the pressure is at 110 N/mm.

The fibrous web receives a high tensile strength and integrity due to the compression performed, i.e. a delamination does not occur since a high cohesion is observed in Z direction of the fibrous web.

The embossed fibrous web is then sprayed with a water-latex mixture via a liquid spray device 6.1. In the embodiment, the water-latex mixture contains 96% water and 4% latex (% by weight). These values are to be varied according to expert opinion dependent on the type of latex used and the type of fiber and fiber compression. In addition, the high water content promotes the bond if the water is evaporated, as is known from paper production from fibers. Furthermore, it is significant that the latex only penetrates into the outer zone of the fibrous web due to the high water content in the applied water-latex mixture and due to the filtering effect of the fibrous web and that a latex bond thus only occurs for the fiber zones on the outside. The water penetrates deeper into the fibrous web and ensures a formation of the aforementioned bond.

To control the penetration of the water-latex mixture, a suction device 16.1 is situated below the conveyer belt 13, whereby various penetration depths can be produced by setting the negative pressure.

A synthetic polymer is used as latex, namely an ethylene vinylacetate copolymer as an aqueous emulsion which has self-crosslinking groups (e.g. AIRFLEX; Manufacturer Air-Products and Chemical, Allentown, Pa., USA). Depending on the cohesion of the fibrous web, 1 to 5 grams latex in the dry state are sufficient per square meter.

The water is dried by a combined infrared/warm air drier 7.1. The fibrous web is then turned and optionally also sprayed with a water-latex mixture from the back (Reference No. 6.2). In this case also, the penetration depth can be affected by a suction device 16.2. A further drier 7.2 is also provided. This is followed by winding up and packaging in the usual manner via a winding device 8, 9.

After the drying, precipitation and cross-linking of the latex, almost no further dust formation due to fibers, fiber scraps, SAP granules and dust which emerge from the fiber zone is observed. In addition, the furnishing with latex facilitates a flexible behavior of the fibrous web that tends to crease so greatly, as is desired especially for the zigzag placement of the fibrous web, whereby this is required for a space-saving form of packaging.

In comparison to similar products found on the market, the dust formation is reduced by 90% and more.

Figure 2:
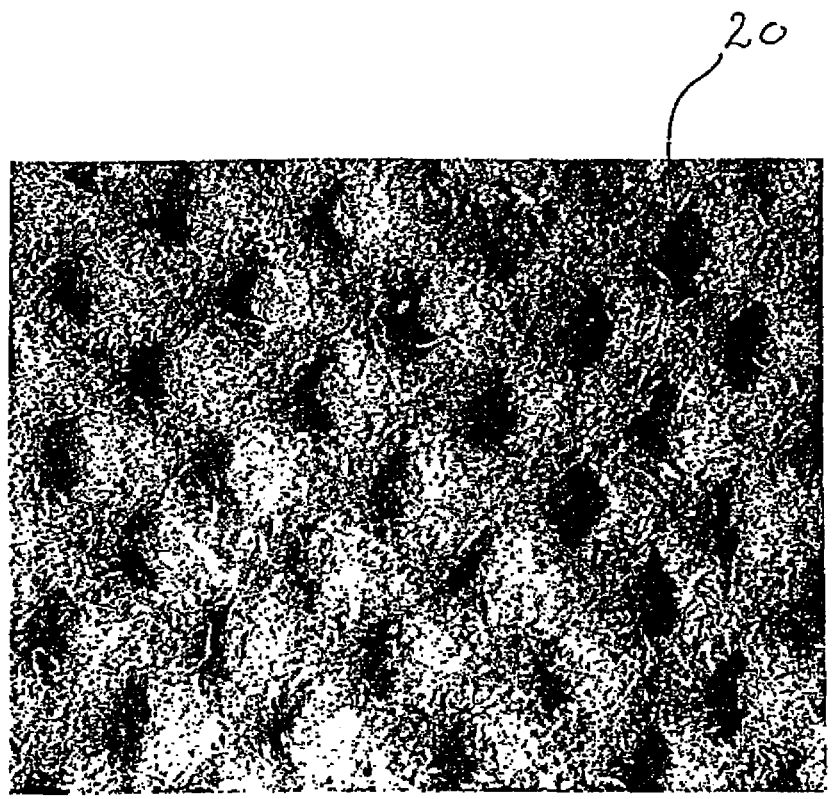
FIG. 2 is a micrograph of a section of the web manufactured in accordance with the invention.

FIG. 2 shows dark and light zones of a fibrous structure in an elevenfold enlargement, as is produced for a fibrous web according to the invention following the operational steps. The dark zones 20 are the impressions of the toothed rolls and, at the same time, zones in which latex, which is dark-coloured here, appears on the surface. It can be seen that a plane, non-continuous wetting is produced by latex. The wetting is per se coherent, however, not continuous for certain surfaces that lie parallel to the upper side, so that a good absorbency of the fibrous web is preserved. The compressed fiber bond zones 10, in which the thickness of the fibrous web is substantially reduced, can also be seen.

FIGS. 3 and 4 show screen-microscopic photographs of the bond zones 20 from which the self-bonding of the fibers can be seen which are squeezed by the high pressure of the rolls. FIG. 3 has a fiftyfold enlargement and shows the total pressure point, whereas FIG. 4 only shows a part of a bond zone with a 500-fold enlargement.

The fibers used in the experiments are so-called fluff pulp (from Weyerhaeuser or Tartas). Similar pictures result with the use of other natural fibers, such as cotton or chemically, thermically or mechanically modified cellulose which can also be used. The use of superabsorbent polymers can also be omitted.

To compare the dust separation "linting" with other products, comparative tests were conducted. A fibrous web VE 150.200 (without SAP) was compared with a fibrous web VE 150.202 (with SAP) as well as with two fibrous webs from absorption cores of cellulose airlaid material which were removed from underwear liners, so-called panty liners. The following table shows the test results:

TABLE 1

|  | VE 150.200 | VE 150.202 | Compar. 1 | Compar. 2 |
|---|---|---|---|---|
| Areal weight in $g/m^2$ | 150 | 150 | 250 | 200 |
| SAP content (%) | 0 | 15 | 23 | 30 |
| Dust content (%) | 0.0541 | 0.0782 | 0.898 | 0.311 |

As can be seen in the table, a low degree of dust development is obtained in the samples produced according to the invention.

Even in the case where synthetic polymers are used as latex, it is still possible to obtain a compostability due to the low content of these polymers. Of course, this also depends on the type of superabsorbent polymer used. However, it is also possible in this case to use SAP that is compostable (trade name: Lysorb and Sorbfresh (especially suitable for food absorbing liners, Manufacturer Lysac Technologies Inc., Canada).

The tensile strength according to the measuring method EDANA 20.02.89 is about 20 N per 50 mm web width after drying, whereby a part of the strength can be attributed to the latex coating. Aqueous emulsions with vinyl acetate, acrylic ester polymers, ethylene vinyl acetate copolymers, styrene butadiene caproxylate copolymers and polyacryl nitrile are suitable as latices. Starch-based latices (e.g.: StructureCote of Vinamul-Polymers) are used as degradable latices.

The end product has a tensile strength that makes it suitable for use in hygiene products. In comparative tests according to the following Table 2, it was moreover ascertained that a slight back-wetting (wetback) occurs when wetting with a 7 ml sodium chloride solution having 0.9% by weight salt content and diffusion on a surface with 200 $cm^2$. Airlaid hybrid products in which the cellulose fibers are bound with molten bicomponent fibers and have a latex spray layer, showed a high back-wetting. The improved moisture absorption of the products produced according to the invention is obviously due to the non-continuous wetting by the bonding latex.

TABLE 2

|  | VE 150.200 | VE 150.202 | A 150 $g/m^2$ | B 185 $g/m_2$ | C 150 $g/m^2$ |
|---|---|---|---|---|---|
| Bonding | Accdg. to invention | Accdg. to invention | Hybrid | Hybrid | Hybrid |
| SAP content % | 0 | 15 | 15 | 10 | 20 |
| Back-wetting in grams | 0.0108 | 0.0116 | 0.0817 | 0.168 | 0.0536 |

Further examples of applications can be found in the following Table 3 which shows examples of mixtures for specific applications. It should thereby be stressed that the latex constituent at higher areal weights is reduced, while the water constituent used remains the same in relation to the dried end product. This is realized by a stronger dilution of the latex-water mixture. For example, a latex-water mixture of 6 to 8% by weight latex can be used with 92 to 94% by weight water in the version (see Table 3) with an areal weight of 120 $g/m^2$. In the fibrous web having an areal weight of 500 $g/m^2$, a dispersion with 2 to 4% by weight latex can be sprayed on. The amount of the water applied is important since, when it evaporates, the water produces hydrogen bonds between the cellulose fibers.

TABLE 3

| Examples of applications | Areal weight in $g/m^2$ (after drying) | Fibers (fluff pulp) | | SAP, preferably in form of SAF* | | Latex | |
|---|---|---|---|---|---|---|---|
|  |  | % | $g/m^2$ | % | $g/m^2$ | % | $g/m^2$ |
| Underwear liners, food-absorbent liners | 120 | 82 | 98.4 | 15 | 18 | 3 | 3.6 |
| Thin hygiene absorbent liners; food absorbent liners | 200 | 68 | 136 | 30 | 60 | 2 | 4 |
| Disposable diapers | 500 | 49 | 245 | 50 | 250 | 1 | 5 |

*SAF = superabsorbent fibers

I claim:

1. A method for producing a fibrous web suitable for the production of hygiene articles, in particular for incontinence articles, disposable diapers, panty liners or sanitary napkins, or absorbent liners, the fiber content of which consists essentially of cellulose fibers of natural origin, said method being an air-laid process comprising the following procedural steps:

a) forming an essentially uniformly thick, dry fiber layer from loose fibers having a low moisture content that is in the range of residual moisture, said layer exhibiting a thickness;

b) embossing the fiber layer to obtain a fibrous web and forming an embossed pattern with compressed fiber bond zones in which the fibers are essentially interconnected and self-bonding, while preserving said thickness;

c) moistening the fibrous web with a water-latex mixture on at least one of the outer zones, the water-latex mixture containing 95 to 99% by weight water and 5 to 1% by weight latex thereby forming a hydrogen bond between fibers in said fibrous web; and d) after the step of embossing, precipitating the latex by drying while bonding the fibers inside and outside the fiber bond zones, whereby the resulting fibrous web exhibits dust due to fluff less than 0.1%, and whereby the mass of latex bound with the fibrous web is 1 to 5 g/m² in the dry state, and the resulting fibrous web contains 1% to 3% per weight [or less] latex.

2. The method according to claim 1, characterized in that the areal weight of the dried fibrous web is set to a range of between 20 and 500 g/m2.

3. The method according to claim 2, characterized in that the areal weight of the dried fibrous web is set to a range of between 100 and 200 g/m².

4. The method according to claim 1, characterized in that the upper and lower side of the web are moistened with the water-latex mixture in successive steps.

5. The method according to claim 2, characterized in that, during and/or after moistening of the fibrous web, the penetration of the moisture into the fibrous web is controlled with aid of a negative pressure applied to the fibrous web.

6. The method according to claim 1, characterized in that the embossing of the fiber layer takes place in a press roll arrangement, whereby at least one roll is a toothed roll.

7. The method according to claim 1, characterized in that, dependent on the areal weight of the fiber layer, different embossing pressures in the range of 30 N/mm to 120 N/mm line pressure are applied.

8. The method according to claim 1, characterized in that superabsorbent polymers (SAP), as superabsorbent fibers, are added to the fiber layer or the fibrous web prior to embossing.

9. The method according to claim 8, characterized in that the superabsorbent polymers (SAP), are inserted in the fiber layer while said fiber layer is being formed.

10. The method according to claim 8, characterized in that superabsorbent polymers (SAP) are added in homogeneous distribution to the cellulose fibers prior to laying the fibers.

11. The method according to claim 8, characterized in that the superabsorbent polymers (SAP) are superabsorbent fibers.

12. The method according to claim 11, characterized in that the superabsorbent fibers are inserted in the fiber layer while forming layers.

13. The method according to claim 11, characterized in that superabsorbent fibers are added in homogeneous distribution to the cellulose fibers prior to laying the fibers.

14. The method according to claim 1, characterized in that 16 to 49 compressed fiber bond zones are inserted per cm2 of the fibrous web.

15. The method according to claim 1, characterized in that the compressed fiber bond zones each cover an area of 0.03 to 1 mm².

16. The method according to claim 1, characterized in that the water-latex mixture is applied with aid of rolls as a foam coating or by spraying.

17. The method according to claim 1, characterized in that the drying of the water for precipitating the latex takes place with aid of radiant heat or by blowing warm air through the fibrous web.

18. The method according to claim 1, characterized in that a biologically degradable latex, that is a starch-based latex, is used.

19. The method according to claim 1, characterized in that, after precipitation and drying, the latex on at least one side of the fibrous web is hydrophilic.

20. The method according to claim 1, characterized in that different latices are used for the opposite sides of the fibrous web.

21. The method according to claim 20, characterized in that, after precipitation and drying, the latex on the one side of the fibrous web is hydrophilic and hydrophobic on the other side.

22. A fibrous web that is suitable for manufacturing hygiene articles, wherein said web has a degree of dust of less than 0.1%, and wherein said web is produced by:

a) forming an essentially uniformly thick, dry fiber layer from loose fibers having a low moisture content that is in the range of residual moisture, said layer exhibiting a thickness and sufficiently self supporting to support web transfer to an embossing station;

b) embossing the fiber layer to obtain a fibrous web and forming an embossed pattern with compressed fiber bond zones in which the fibers are essentially interconnected and self-bonding, c) moistening the fibrous web with a water-latex mixture on at least one of the outer zones, the water-latex mixture containing 95 to 99% by weight water and 5 to 0.1% by weight latex thereby forming a hydrogen bond between fibers in said fibrous web; and d) precipitating the latex by drying while bonding the fibers inside and outside the fiber bond zones, and whereby dust due to fluff less than 0.1% and the mass of the latex bound with the fibrous web is 1 to 5 g/m² in the dry state, and the resulting fibrous web contains 1% to 3% per weight or less latex.

* * * * *